United States Patent [19]  [11] 4,105,788
Jones et al.  [45] Aug. 8, 1978

[54] DIACYLATED DERIVATIVES OF γ-GLUTAMYL DOPAMINE

[75] Inventors: Peter Hadley Jones, Lake Forest; Carroll Wayne Ours, Zion; Jaroslav Kyncl, Lake Bluff, all of Ill.

[73] Assignee: Abbott Laboratories, North Chicago, Ill.

[21] Appl. No.: 793,468

[22] Filed: May 3, 1977

Related U.S. Application Data

[62] Division of Ser. No. 612,511, Sep. 11, 1975, Pat. No. 4,031,242.

[51] Int. Cl.² ............... A61K 31/24; C07C 101/24
[52] U.S. Cl. .................................................. 424/309
[58] Field of Search ............... 560/41, 39; 260/404.5; 424/309

[56] References Cited

U.S. PATENT DOCUMENTS

| | | | |
|---|---|---|---|
| 3,676,492 | 7/1972 | Biel et al. | 260/559 A |
| 3,891,696 | 6/1975 | Bador et al. | 260/519 |
| 3,903,147 | 9/1975 | Kyncl et al. | 260/519 |
| 3,907,864 | 9/1975 | Biel et al. | 560/41 |
| 3,910,988 | 10/1975 | Jones et al. | 260/404.5 A |
| 4,017,636 | 4/1977 | Jones | 424/309 |

Primary Examiner—James O. Thomas, Jr.
Assistant Examiner—G. T. Breitenstein
Attorney, Agent, or Firm—Paul D. Burgauer; Robert L. Niblack

[57] ABSTRACT

This invention covers diacylated derivatives of γ-glutamyl dopamine selected from the group consisting of

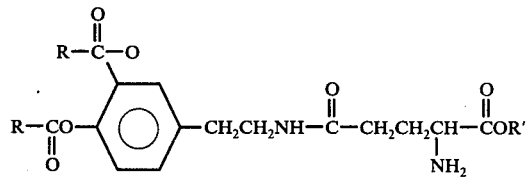

where R is a $C_1$-$C_{12}$ straight or branched chain alkyl radical, a phenyl ring or a substituted phenyl ring and R' is H or a $C_1$-$C_7$ alkyl, and a pharmaceutically acceptable acid addition salt thereof.

The compounds of this invention are useful to increase the renal blood flow by being administered to warm-blooded animals by clinically accepted routes of administration such as oral, parenteral, rectal and the like.

8 Claims, No Drawings

DIACYLATED DERIVATIVES OF γ-GLUTAMYL DOPAMINE

This is a division of application Ser. No. 612,511 filed Sept. 11, 1975, now U.S. Pat. No. 4,031,242.

BACKGROUND OF THE INVENTION

Dopamine has been reported as being useful in treating congestive heart failure and shock. In addition, certain amino acid amides of dopamine have been found useful as renal vasodilators and antihypertensive agents, (for example, see U.S. Pat. No. 3,676,492). However, compounds disclosed in the just mentioned patent and others which are used as renal vasodilators have the disadvantage of low potency upon oral administration.

Most of the dopamine, or dopamine generating compound is not utilized to produce the desired activity because it is inactivated too rapidly by metabolic processes in the warm-blooded organisms. While the amount of dopamine necessary to produce the renal vasodilation is rather small, a great quantity of the dopamine or dopamine-generating compound have to be administered to provide for the large metabolic wastage.

It would be a distinct advance in the art if a compound could be protected chemically against the rapid metabolic degradation, since it presumably would decrease the amount of the compound to be administered to produce the pharmacological effect.

DETAILED DESCRIPTION OF THE INVENTION

The present invention relates to derivatives of γ-glutamine dopamine which are useful as renal vasodilators. More particularly, the present invention provides diacylated derivatives of γ-glutamyl dopamine selected from the group consisting of

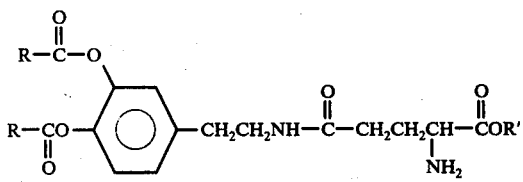

where R is a $C_1$-$C_{12}$ straight or branched chain alkyl radical, a phenyl ring or a substituted phenyl ring and R' is H or a $C_1$-$C_7$ alkyl, and a pharmaceutically acceptable acid addition salt thereof.

The compounds of the present invention may be prepared according to the following reaction scheme I(a):

Scheme I(a)

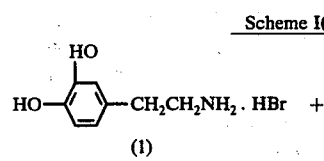

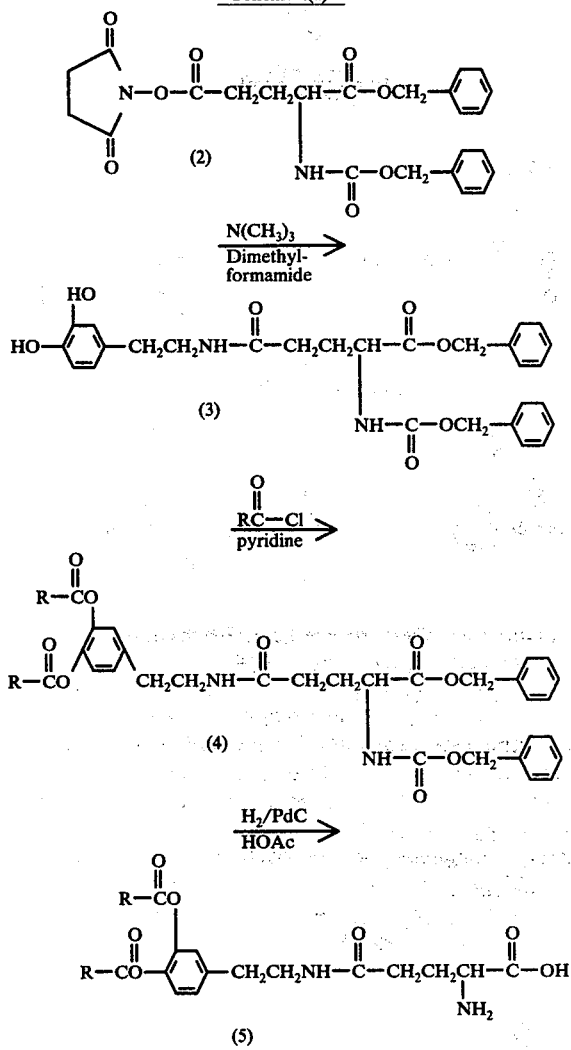

The present compounds may be made by the alternate reaction of scheme I(b):

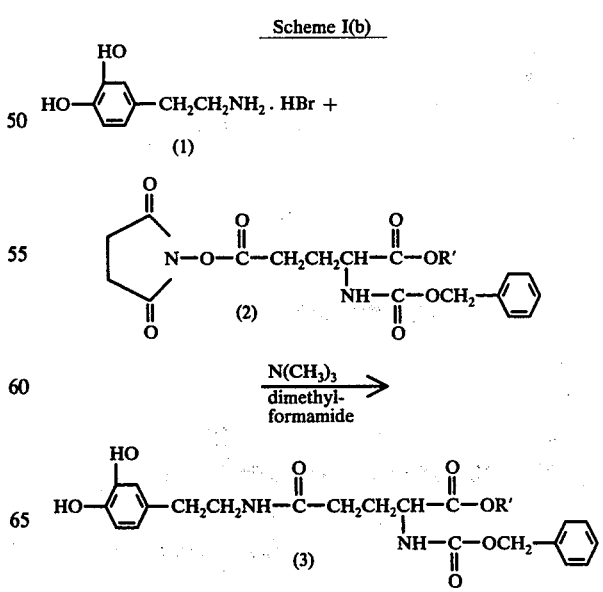

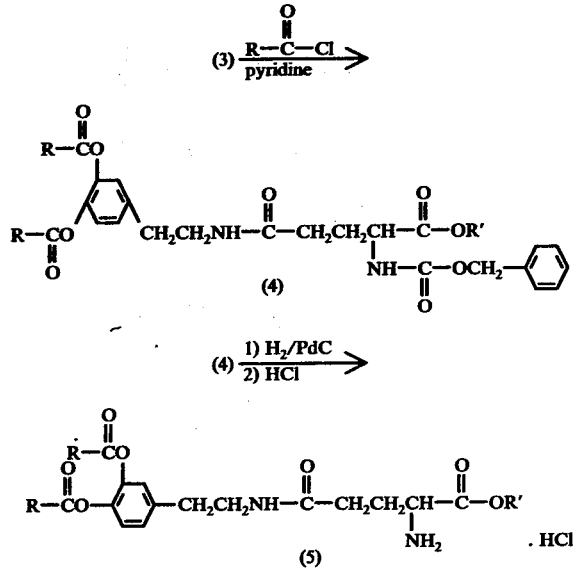
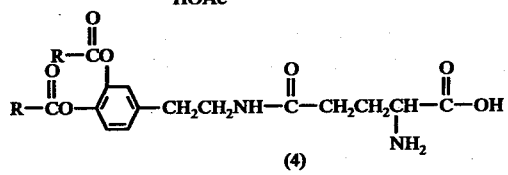

Scheme I(a) differs from Scheme I(b) by the fact that when the benzyl ester is used, catalytic hydrogenation of the N-carbobenzoxy group is accompanied by hydrogenolysis of the benzyl ester producing the amino acid. When other esters are used, this does not occur thereby allowing the preparation of the amino acid esters which are isolated as stable hydrogen chloride salts.

The benzyl ester and other alkyl esters of N-CBZ-γ-glutamyl dopamine are described in U.S. Pat. Nos. 3,903,147 and 3,910,988.

The present compounds may also be made according to the reaction scheme (II):

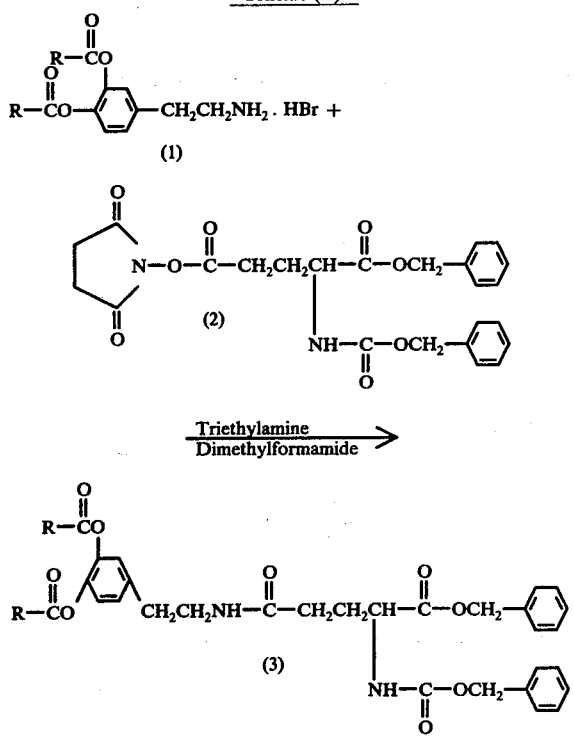

In scheme (II) the phenolic hydroxyls are acylated before coupling with the active ester, (2), whereas in scheme I(a) and I(b), the hydroxyls are acylated after the coupling step.

The general procedures for schemes (I) and (II) are:

Scheme (I)

The N-CBZ-L-[$N^5$-β-(3,4-dihydroxyphenyl)ethyl]-glutamine O-alkyl ester was taken up in pyridine and treated with 2.2 eg. of an acylating agent. This mixture was stirred at room temperature (or heated at reflux) for 16 hours. The solvent was removed in vacuo to give a semisolid residue. This was treated with water to give a solid (or an oil). The solid was recrystallized from a suitable solvent. If an oil, it was extracted with ethyl acetate, washed with 1N HCl, 1, water saturated NaHCO$_3$ and finally water. The ethyl acetate layer was dried over anhydrous sodium sulfate and concentrated in vacuo and gave an oil (or a solid). This product could be purified by chromatography or by recrystallization (if a solid).

Preparation of [$N^5$-β-(3,4-Diacyloxyphenyl)ethyl]-glutamine

The protected amide (oil or solid) was reduced in a Parr apparatus in glacial acetic acid containing 5% Pd.C catalyst. After uptake of hydrogen was complete, the catalyst was filtered and concentrated in vacuo to give a solid. This solid was filtered and washed with ethyl ether to give the product. The product was in many cases analytically pure. If recrystallization was required it was recrystallized from a suitable solvent.

Scheme (II)

The active ester of N-CBZ-L-glutamic acid α-alkyl ester, (1.0 eq.) was dissolved in a minimum of dimethylformamide. The 3,4-diacylated dopamine hydrobromide (1.0 eq.) was added. To this stirred solution was added 1.5 eq. of triethylamine. The reaction mixture was stirred at room temperature for 4 hours, diluted with cold water to give an oil. The oil in many cases solidified. The oil was extracted with ethyl acetate, washed with water, dilute acid, sodium bicarbonate, and water. Dried over sodium sulfate and concentrated in vacuo to give an oil. The oil could be purified by chromatography. If the product was a solid, it was purified by crystallization.

The derivatives of γ-glutamyl dopamine of the present invention may be used in increasing the renal blood flow in warm-blooded animals by administering to said animals at least an effective amount of the above derivative of γ-glutamyl dopamine. The medicinal composition that is administered to warm-blooded animals to increase the renal blood flow is a composition comprising the derivative of γ-glutamyl dopamine as the active portion, together with a pharmaceutically acceptable carrier. The compounds of the present invention may be prepared by a wide variety of methods. Generally, the preferred method by which the present compounds are made includes initially coupling dopamine. hydrochloride with a γ-activated ester of a suitably protected glutamic acid derivative, (e.g., N-CBZ-L-glutamic acid α-benzyl ester) in the presence of a base (e.g., pyridine or triethylamine), and then acylating the mixture with a suitable acylating agent such as acetyl chloride, acetic anhydride or another acyl chloride or acyl bromide. The protecting groups are then removed by known methods such as by catalytic hydrogenation to provide the desired compound.

By acylating the catechol hydroxyls, this will increase the renal vasodilating activity of the warm-blooded animal to which it is administered. This is probably due to blocking the sulfitase enzymes in the intestinal wall allowing for better absorption of the drug.

The following examples will provide further illustrations of the procedure for making the compounds of the present invention and will serve to show the advantages and effectiveness of the present compounds as renal vasodilating agents.

EXAMPLE I

Preparation of
N-CBZ-[$N^5$-β-(3,4-Dihydroxyphenyl)Ethyl]-Glutamine O-Benzyl Ester A solution of N-CBZ-$O^5$-Succimimido-L-glutamic acid O-benzyl ester (0.1 mole, 46.8 g.) and dopamine.HBr (0.1 mole, 23.4 g.) in 100 ml. of dimethyl formamide was stirred and treated in one portion with triethylamine (0.15 mole, 21 ml.). This mixture was stirred at room temperature for 4 hours. The mixture was concentrated to approximately 50 ml. and then diluted with water to give an oil. This oil was extracted with 3 × 100 ml. portions of ethyl acetate, washed successively with 100 ml. water, 100 ml. 1N HCl, 1, 100 ml. water, 100 ml. saturated NaHCO$_3$ and finally 100 ml. water. The ethyl acetate layer was dried over anhydrous sodium sulfate and concentrated in vacuo to give an oil. This oil slowly solidified. This product 48 g. (96%), m.p. 105°–8° was used in the next step without further purification.

EXAMPLE II

Preparation of
N-CBZ-[$N^5$-β-(3,4-diacetoxyphenyl)ethyl]-Glutamine O-Benzyl ester To a solution of N-CBZ-[$N^5$-β-(3,4-dihydroxyphenyl)ethyl]-glutamine O-benzyl ester (0.01 mole, 5.06 g.) in 50 ml. pyridine was treated dropwise with stirring with acetic anhydride (0.03 mole, 3.1 g.). This was stirred at room temperature overnight (approx. 16 hours). The solvent was removed to give a semisolid mass. This was triturated with water to give an oil, which was extracted with ethyl acetate, dried over anhydrous sodium sulfate. The solvent was removed in vacuo to give an oil. The oil was taken up in ether and allowed to crystallize to give a white solid, 4.5 g. (76%), m.p. 120°–2°. Microanalysis for C$_{32}$H$_{34}$N$_2$O$_9$ = 590.636 g./mole.

| Calc. % | | Found % | |
|---|---|---|---|
| C | 65.08 | C | 64.79 |
| H | 5.80 | H | 5.80 |
| N | 4.74 | N | 4.89 |

EXAMPLE III

Preparation of
[$N^5$-β-(3,4-diacetoxyphenyl)ethyl]-Glutamine

A suspension of the protected amide in Example II, (0.012 mole, 7.0 g.) was reduced in a Parr apparatus in glacial acetic acid containing 1.2 g. 5% Pd.C catalyst. The catalyst was filtered. The filtrate was concentrated in vacuo to give a solid. This white solid was collected, washed with ethyl ether and dried in vacuo to give 4.0 g. (91%) m.p. 169°–71°. Microanalysis for C$_{17}$H$_{22}$N$_2$O$_7$ = 366.37 g./mole.

| Calc. % | | Found % | |
|---|---|---|---|
| C | 55.73 | C | 55.41 |
| H | 6.05 | H | 6.16 |
| N | 7.65 | N | 7.58 |

EXAMPLE IV

Preparation of
N-CBZ-L-[$N^5$-β-(3,4-Dibenzoyloxyphenyl)ethyl]-Glutamine O-Benzyl Ester A solution of N-CBZ-[$N^5$-β-(3,4-dihydroxyphenyl)ethyl]-glutamine O-benzyl ester, (0.02 mole, 10.2 g.) was dissolved in 50 ml. pyridine. This solution was treated dropwise, with stirring, with benzoyl chloride (0.05 mole, 7.0 g.). Stirred for 16 hours at room temperature, concentrated in vacuo to give a solid. This was filtered with the aid of water and air dried to give 12.0 g. product, m.p. 125°–150°. Recrystallized twice from ethanol to give 7.4 g. (52%), m.p. 165°–7°. Microanalysis for C$_{42}$H$_{38}$N$_2$O$_9$ = 714.779.

| Calc. % | | Found % | |
|---|---|---|---|
| C | 70.58 | C | 70.29 |
| H | 5.36 | H | 5.35 |
| N | 3.92 | N | 3.96 |

EXAMPLE V

Preparation of
L-[$N^5$-β-(3,4-dibenzoyloxyphenyl)ethyl]-Glutamine

A suspension of the protected amide from Example IV, (8.3 mmole, 6.0 g.) was reduced in a Parr apparatus in glacial acetic acid containing 1.0 g. (5%) Pd.C catalyst. After uptake of hydrogen was complete, the catalyst was filtered. The filtrate was concentrated in vacuo to give 4.3 g. product, m.p. 150°–160° C. This solid was crystallized from methanol to give 2.0 g. (50%), m.p. 171°–173°. Microanalysis for C$_{27}$H$_{26}$N$_2$O$_7$ · ½ H O = 499.517 g./mole.

| Calc. % | | Found % | |
|---|---|---|---|
| C | 64.92 | C | 64.72 |
| H | 5.45 | H | 5.24 |
| N | 5.61 | N | 5.50 |

EXAMPLE VI

Preparation of
N-CBZ-L-[N$^5$-(3,4-dihydroxyphenyl)ethyl]-Glutamine O-Ethyl Ester A solution of the active ester (Example I, U.S. Ser. No. 408,901), (approx. 0.1 mole, 41 g.) in 150 ml. dimethyl formamide was treated with dopamine .HCl (0.1 mole, 37 g.) and to this solution was added triethylamine (0.15 mole, 21 ml.). This mixture was stirred for 4 hours at room temperature, concentrated to 75 ml. volumn in vacuo and treated with water to give an oil. This oil was extracted with ethyl acetate, washed with water, dried over anhydrous sodium sulfate and concentrated to give a viscous oil. This oil was not purified further but used in the following example without further purification.

EXAMPLE VII

Preparation of
N-CBZ-L-[N$^5$-(3,4-diacetoxyphenyl)ethyl]-Glutamine O-Ethyl Ester The oil from Example VI, (0.1 mole, 44 g.) was dissolved in 200 ml. pyridine and treated with stirring with acetic anhydride (0.25 mole, 25 g.). This solution was stirred at room temperature for 16 hours, concentrated to give a semisolid mass. The residue was treated with water to give an oil. The oil was extracted with ethyl acetate, concentrated in vacuo after drying over sodium sulfate to give 47.2 g. of an oil.

EXAMPLE VIII

Preparation of
[N$^5$-$\beta$-(3,4-Diacetoxyphenyl)Ethyl]-Glutamine O-Ethyl Ester Hydrochloride A solution of the protected amide from Example VII (0.05 mole, 27 g.) in glacial acetic acid was reduced in a Parr apparatus with 5.0 g., 5% Pd.C. After uptake was complete, the catalyst was filtered. The filtrate was concentrated in vacuo to give an oil. The oil was treated with etherial hydrogen chloride to give on evaporation of the ether a glass-like solid. Yield of glass was 20 g. (91%).

EXAMPLES IX – XIII

Similarly were prepared [N$^5$-$\beta$-(3,4-trimethylacetoxyphenyl)ethyl]-glutamine, amorphous glass; [N$^5$-$\beta$-(3,4-dibutyryloxyphenyl)ethyl]-glutamine, m.p. 162°–5°; [N$^5$-$\beta$-(3,4-dihexanoyloxyphenyl)ethyl]-glutamine, m.p. 172°–4°; [N$^5$-$\beta$-(3,4-didodecanoyloxyphenyl)ethyl]-glutamine, m.p. 175°–7°; and [N$^5$-$\beta$-(3,4-diphenylactoxyphenyl)ethyl]-glutamine, m.p. 146°–150°.

EXAMPLE XIV

Preparation of
N-CBZ-[N$^5$-$\beta$-(3,4-Diacetoxyphenyl)Ethyl]-Glutamine O-Benzyl Ester A solution of 3,4-diacetyldopamine hydrobromide, (0.01 mole, 3.2 g.) and N-CBZ-O$^5$-succinimido-L-glutamic acid O-benzyl ester (0.01 mole, 4.7 g.) in 50 ml. dimethyl formamide was stirred and treated in one portion with triethylamine (0.02 mole, 2.8 ml.). This mixture was stirred at room temperature for 2 hours. The mixture was concentrated to about 25 ml. volume at 40°–45° in vacuo. The residual mass was treated with water to give an oil that solidified on standing. This solid was collected and washed with water. Drying in vacuo gave 4.7 g., m.p. 70°–75°. This solid was purified by recrystallizing from ether to give 3.8 g. product, m.p. 119°–21°. Thin layer chromatography showed the product to be identical to the product in Example II.

EXAMPLE XV

Effect of Derivatives of γ-Glutamyl Dopamines On Renal Blood Flow in Unanesthetized, Instrumented Dogs Tests were made to determine the effect of the various derivatives of γ-glutamyl dopamine compounds on the renal blood flow in unanesthetized instrumented Beagle dogs.

The dogs used in this test were trained to lie quietly on the dog table. On the day of surgery, an electromagnetic flow probe (Caroline Medical Electronics) was implanted, under anesthesia, around the renal artery, and the connecting cable was brought outside in the neck area. A special silastic-covered polyethylene catheter was implanted into the abdominal aorta via the right femoral artery for recording the blood pressure. The other end of this catheter was exteriorized in the neck area next to the flow probe connector. The dogs were allowed to recover from the anesthesia. At least 4 days elapsed between the surgery and the drug testing.

For the drug testing, the dogs were placed on the table, and the renal blood flow was monitored in the unanesthetized state. In some cases, the effect of the drug was so potent and prolonged that it exceeded the duration which was considered to be reasonable to keep the conscious dog on the restraining table, and was not further recorded.

The results of the test are recorded in the table below, Table I. In addition, there are other compounds which were tested on the unanesthetized dogs as described above. The drugs were administered to the animals by gavage or orally in a gelatin capsule. Throughout the period of drug testing, placebo was tested occasionally, which consisted of 20–100 ml. of water or an empty gelatin capsule and which was always devoid of any effects.

The compounds used in this test are:

1. [N$^5$-$\beta$-(3,4-diacetoxyphenyl)ethyl]-glutamine
2. [N$^5$-$\beta$-(3,4-di-trimethylacetoxyphenyl)ethyl]-glutamine
3. [N$^5$-$\beta$-(3,4-dihydroxyphenyl)ethyl]-glutamine O-hexyl ester hydrochloride
4. [N$^5$-$\beta$-(3,4-dihydroxyphenyl)ethyl]-glutamine O-ethyl ester hydrochloride
5. N-L-isoleucyl-$\beta$-(3,4-dihydroxyphenyl)ethylamine hydrochloride Compounds 3, 4 and 5 are known, with compounds 3 and 4 being described in U.S. application Ser. No. 408,901 and compound 5 being described in U.S. Pat. No. 3,903,077. Compounds 1 and 2 are of the present invention.

The progress and development of a potent orally active renal vasodilator can be best appreciated by reading Table I, below, from Compound 5 to 1.

Since all the compounds were administered in doses equimolar to those of dopamine, the comparison of the efficacy of these compounds is considered reasonable.

While compound 4 represents an improvement in its duration of action over compound 5, the activity of compound 3 exceeded that of compound 4 by being active at a lower dose.

However, compound 2 and, in particular, compound 1 are superior to all previous compounds by their extraordinary potency which is apparent at dosages where all previous compounds are inactive.

The results of the tests are recorded below in Table I:

TABLE I

Effects of Drugs on Renal Blood Flow (RBF) In Unanesthetized Instrumented Dogs

| ORAL DOSE (DA mg/kg)* | Compound 1 | | Compound 2 | |
|---|---|---|---|---|
| | RBF PEAK INCREASE (percent) | DURATION (min) | RBF PEAK INCREASE (percent) | DURATION (min) |
| 15.0 | | | | |
| 5.0 | | | | |
| 1.5 | 50.5 | 228 | 33.7 | 180 |
| | 80.4 | >360 | 70.7 | >330 |
| | 32.2 | >360 | 39.1 | >330 |
| | 42.0 | >390 | 13.4 | >330 |
| | 51.3 ± 10.4** | | 39.2 ± 11.9 | |
| 0.5 | 66.3 | >301 | 9.0 | 94 |
| | 31.2 | 147 | 52.1 | >240 |
| | 36.6 | >330 | 6.2 | 90 |
| | 75.0 | >395 | 13.7 | 40 |
| | 17.2 | >270 | 20.3 ± 10.7 | |
| | 45.3 ± 10.9 | | | |

| ORAL DOSE (DA mg/kg)* | Compound 3 | | Compound 4 | | Compound 5 | |
|---|---|---|---|---|---|---|
| | RBF PEAK INCREASE (percent) | DURATION (min) | RBF PEAK INCREASE (percent) | DURATION (min) | RBF PEAK INCREASE (percent) | DURATION (min) |
| 15.0 | 30.5 | 215 | | | | |
| | 97.0 | 295 | | | | |
| | 87.0 | >332 | 65.6 + 7 | 271.6 ± 54.7 | 90.8 ± 21.5 | 141.1 ± 18.4 |
| | 43.9 | 267 | | | | |
| | 64.6 ± 16.2 | | | | | |
| 5.0 | 71.0 | >270 | | | (7.5 DA mg/kg) | |
| | 33.9 | >270 | 30.0 ± 4.2 | 125.2 ± 4.7 | 94.7 ± 7.2 | 92.0 ± 17.2 |
| | 39.4 | >279 | | | | |
| | 34.2 | 156 | | | | |
| | 44.6 ± 8.9 | | | | | |
| 1.5 | 9.7 ± 2.1 | 80.5 ± 36 | 16.8 ± 4.2 | 75.7 ± 11.2 | | |
| 0.5 | | | | | | |

*(DA mg/kg) - All compounds were administered in doses equimolar to those of dopamine.
**Mean ± S.E.M.
+In some experiments the duration of the effect exceeded the actual time of observation and is denoted by >.

We claim:

1. A diacylated derivative of γ-glutamyl dopamine selected from the group consisting of

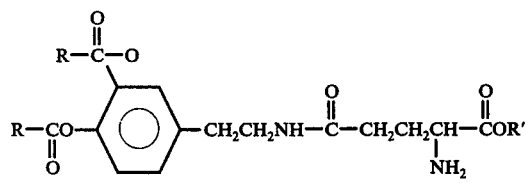

where R is a $C_1$–$C_{12}$ straight or branched chain alkyl radical, and R' is a $C_1$–$C_7$ alkyl, and a pharmaceutically acceptable acid addition salt thereof.

2. A derivative according to claim 1 which is a hydrochloride salt.

3. A derivative according to claim 1, wherein R is $CH_3$ and R' is $C_2H_5$.

4. A derivative according to claim 3, [$N^5$-β-(3,4-diacetoxyphenyl)ethyl]-glutamine O-ethyl ester hydrochloride.

5. A method of increasing renal blood flow of warm-blooded animals which comprises administering to said mammals at least an effective amount of a renal vasodilator compound comprising a diacylated derivative of γ-glutamyl dopamine selected from the group consisting of

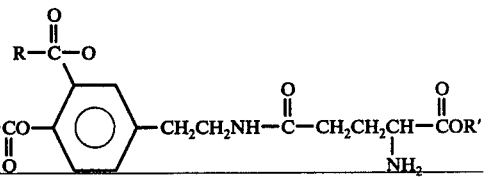

where R is a $C_1$–$C_{12}$ straight or branched chain alkyl radical, and R' is a $C_1$–$C_7$ alkyl, and a pharmaceutically acceptable acid addition salt thereof.

6. The method of claim 5, wherein said salt is a hydrochloride salt.

7. A pharmaceutical composition in unit dosage form effective in increasing renal blood flow which comprises an active portion comprising a diacylated derivative of γ-glutamyl dopamine selected from the group consisting of

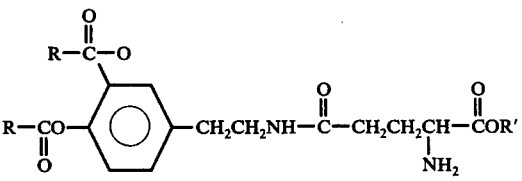

where R is a $C_1$–$C_{12}$ straight or branched chain alkyl radical, and R' is a $C_1$–$C_7$ alkyl, and a pharmaceutically acceptable carrier.

8. The composition of claim 7 wherein said derivative is a hydrochloride salt.

* * * * *